United States Patent [19]
Caron et al.

[11] Patent Number: 5,992,215
[45] Date of Patent: Nov. 30, 1999

[54] SURFACE ACOUSTIC WAVE MERCURY VAPOR SENSORS

[75] Inventors: Joshua J. Caron, Orono; Reichl B. Haskell, Veazie, both of Me.; Carl J. Freeman, Rockville, Md.; John F. Vetelino, Orono, Me.

[73] Assignee: Sensor Research and Development Corp., Orono, Me.

[21] Appl. No.: 08/864,616

[22] Filed: May 29, 1997

[51] Int. Cl.⁶ .......................... G01N 29/00; G01N 29/22; H01L 41/08

[52] U.S. Cl. ...................... 73/24.01; 73/24.06; 73/31.02; 310/313 R

[58] Field of Search ............................... 73/23.31, 24.01, 73/24.06, 31.01, 31.02, 31.03; 310/313 R

[56] References Cited

U.S. PATENT DOCUMENTS

| | | | |
|---|---|---|---|
| 3,795,879 | 3/1974 | Whitehouse et al. | 310/313 R |
| 5,117,146 | 5/1992 | Martin et al. | 73/24.01 X |
| 5,221,871 | 6/1993 | Fuchs et al. | 73/24.01 X |

FOREIGN PATENT DOCUMENTS

| | | | |
|---|---|---|---|
| 268530 | 5/1989 | Germany . | |
| 6-258210 | 9/1994 | Japan | 73/24.01 |

OTHER PUBLICATIONS

Puk et al., "Critical Review of Analytical Methods for Determination of Inorganic Mercury and Methylmercury Compunds", Applied Organometallic Chemistry, vol. 08, 1994, pp. 293–302.

Jones et al., "Method Development and Sample Processing of Water, Soil, and Tissue for the Analysis of Total and Organic Mercury by Cold Vapor Atomic Fluorescence Spectrometry", Water, Air, and Soil Pollution, vol. 80, 1995, pp. 1285–1294.

Aceto et al., "Mercury Speciation in Biological Samples", Intern. J. Environ. Anal. Chem., vol. 60, 1995, pp. 1–13.

Schintu et al., "Organomercury Determination in Biological Reference Materials: Application to a Study on Mercury Speciation in Marine Mammals off the Faroe Islands", Ecotoxicology and Environmental Safety, vol. 24, 1992, pp. 95–101.

Rapsomanikis et al., "New Speciation Approaches in the Biogeochemical Cycles of Organometallics in the Environment", Intern. J. Environ. Anal. Chem., vol. 49, 1992, pp. 43–48.

Puk et al., "Determination of Mercury(II), Monomethylmercury Cation, Dimethylmercury and Diethylmercury by Hydride Generation, Cryogenic Trapping and Atomic Absorption Spectrometric Detection", Analytica Chimica Acta, vol. 292, 1994, pp. 175–183.

McNerney et al., "Mercury Detection by Means of Thin Gold Films" Science, vol. 178, Nov. 1972, pp. 611–612.

(List continued on next page.)

*Primary Examiner*—Daniel S. Larkin
*Attorney, Agent, or Firm*—Pierce Atwood; Chris A. Caseiro

[57] ABSTRACT

A surface acoustic wave (SAW) sensor system and associated method for accurately measuring mercury gas concentrations. The sensor includes a SAW device that may be a SAW delay-line oscillator or a SAW resonator. The surface of the piezoelectric substrate of the SAW device includes a material suitable for amalgamation with mercury. Mercury in the gaseous environment is captured with the amalgamating material so as to cause a change in the mechanical and electrical properties on the surface of the device, thereby causing a change in the frequency output of the device. The piezoelectric substrate of the SAW device is preferably coupled to a heater to permit control of the temperature at the surface of the device. The piezoelectric substrate temperature may be regulated to produce a substantial equilibrium of mercury amalgamation/desorption kinetics. Under the conditions provided by the invention, the mercury concentration in the gaseous environment can be determined.

14 Claims, 13 Drawing Sheets

OTHER PUBLICATIONS

Bristow, "An Evaluation of the Quartz Crystal Microbalance as a Mercury Vapor Sensor for Soil Gases", Journal of Geochemical Exploration, vol. 1, 1972, pp. 55–76.

Scheide et al., "Piezoelectric Sensor for Mercury in Air", Environment Science and Technology, vol. 08, No. 13, Dec. 1974, pp. 1097–1099.

Scheide et al., "A Piezoelectric Crystal Dosimeter for Monitoring Mercury Vapor in Industrial Atmospheres", American Industrial Hygiene Association Journal, Dec. 1975, pp. 897–901.

Scheide et al., "A Piezoelectric Crystal Mercury Monitor", American Induistrial Hygiene Association Journal, vol. 39, Sep. 1978, pp. pp. 745–749.

Scheide, The Piezoelectric–Crystal Dosimeter, The Physics Teacher, Jan. 1977, pp. 47–51.

Ho et al., "Determination of Nanogram Quantities of Mercuryin Water with a Gold–Plated Piezoelectric Crystal Detector", Analytica Chimica Acta, vol. 130, 1981, pp. 141–147.

Mogilevski et al., "Measurement of the Concentration of Mercury Vapour in Air Through a Piezoelectric Method", Sensors and Actuators A, vol. 28, 1991, pp. 35–39.

Spassov et al., "Piezoelectric Sorption Sensor for Mercury Vapors in Air Using a Quartz Resonator", Rev. Sci. Instrum., vol. 64, No. 01, Jan. 1993, pp. 225–227.

Lec et al., "Macroscopic Theory of Surface Acoustic Wave Gas Microsensors", 1988 IEEE Ultrasonics Symposium, pp. 585–589.

Caron et al., "Surface Acoustic Wave Substrates for High Temperature Applications", 1996 IEEE International Frequency Control Symposium, pp. 222–227.

Arizona Instrument, Jerome 431–X Mercury Vapor Analyzer.

Auld, B.A., "Acoustic Fields and Waves In Solid," Preface and Chapter 12 Wiley–Interscience Publication, ©1973.

SURFACE ACOUSTIC WAVE MERCURY VAPOR SENSORS

CROSS-REFERENCE TO RELATED APPLICATIONS

Not Applicable.

STATEMENT REGARDING FEDERALLY SPONSORED RESEARCH OR DEVELOPMENT

Not Applicable

AUTHORIZATION PURSUANT TO 37 C.F.R. §1.71 (d)(e)

A portion of the disclosure of this patent document, including appendices, may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to surface acoustic wave mercury vapor sensors, and more particularly to the in situ detection and measurement of low concentrations of gaseous mercury in air using such surface acoustic wave mercury vapor sensors.

2. Description of the Related Art

Mercury, for example, originating from nuclear fuel and weapons production and disposal, fossil fuel combustion, incineration, and industrial processes, is a major environmental pollutant that exists in air, soil and groundwater. Mercury is particularly dangerous since it can bioaccumulate within the food chain and lead to irreversible neurological disorders and other health related problems.

Current techniques that are used to detect mercury require a variety of elaborate separation strategies in conjunction with chromatographic, electrochemical, or spectroscopic methods, such as atomic absorption and emission.

German Patent No. DD 268 530 A1 is an example of current techniques and is generally directed to a method and device for the concentration determination of mercury in gases, and more specifically relates to the quantitative mercury amount determination of gases, as they arise from the $Hg^0$ emission in reduction-ventilation-processes.

The mercury containing gas is brought into contact with a SAW (surface acoustic wave) device. The surface structure of the SAW device is designed such that the surface acoustic wave passes through a gold-plated contact zone on which the mercury is adsorbed as amalgam. Depending on the amalgam content, the propagation velocity of the surface wave changes. This velocity change is a measure for the mercury concentration and is recorded. The regeneration of the SAW device is done by thermal desorption.

From the literature, various other methods for mercury analysis are know, like photometry, fluorescence-, X-ray-, and mass-spectroscopy. Some of these methods are very costly.

Most common is the method of atom absorption (AAS) based on the cold vapor principle. The detection limit of this method is about 0.1 ng Hg/ml. With the usual dimensions of kuvettes, a relatively large sample amount is necessary for this detection limit, where an enrichment by means of a gold trap may be carried out to improve the sensitivity. Here, in order for the analysis, the mercury has to be released again, where thermodynamic and hydrodynamic problems occur, which is disadvantageous.

In the "American Industrial Hygiene Association Journal", 1975, p. 897–901, a mercury detection method is described based on a piezoelectric crystal. Here, the mass loading of a gold-plated longitudinal oscillator is detected as a change in the resonance frequency.

Conventional use of a bulk oscillator limits the sensitivity because of a relatively low operation frequency, since for a given mass of the layer the dynamic mechanical tension on the crystal surfaces is frequency dependent.

Although these techniques may be able to detect mercury, they are not as advantageous as the surface acoustic wave mercury vapor sensors of the present invention, at least in part because they are not appropriate for in situ monitoring, and typically, samples must be collected and shipped to a central processing facility for analysis.

The numbers in brackets below refer to references listed in the Appendix, the teachings of which are hereby incorporated by reference.

Those concerned with these and other problems recognize the need for an improved surface acoustic wave mercury vapor sensors.

BRIEF SUMMARY OF THE INVENTION

The present invention is directed to surface acoustic wave mercury vapor sensors.

The present invention is also directed to the in situ detection and measurement of low concentrations of gaseous mercury in air.

Therefore, an object of the present invention is the provision of an improved surface acoustic wave mercury vapor sensors for the in situ detection and measurement of low concentrations of gaseous mercury in air.

BRIEF DESCRIPTION OF THE SEVERAL VIEWS OF THE DRAWINGS

Other objects, advantages, and novel features of the present invention will become apparent from the following detailed description of the invention when considered in conjunction with the accompanying drawings, wherein.

DETAILED DESCRIPTION OF THE INVENTION

With reference to the drawings to be described herein the present invention intended to be claimed is a surface acoustic wave sensor which includes a surface acoustic wave (SAW) delay line oscillator having a metal-coated delay path or a saw resonator having one or more gold interdigital transducers, and a piezoelectric crystal substrate.

For purposes of the present invention, the substrate comprises a piezoelectric material, and the metal coating comprises any metal with which mercury amalgamates, preferably wherein the metal is selected from the group consisting of gold (Au), silver (Ag), copper (Cu). Most preferably wherein the substrate comprises quartz ($SiO_2$).

Figure 3:
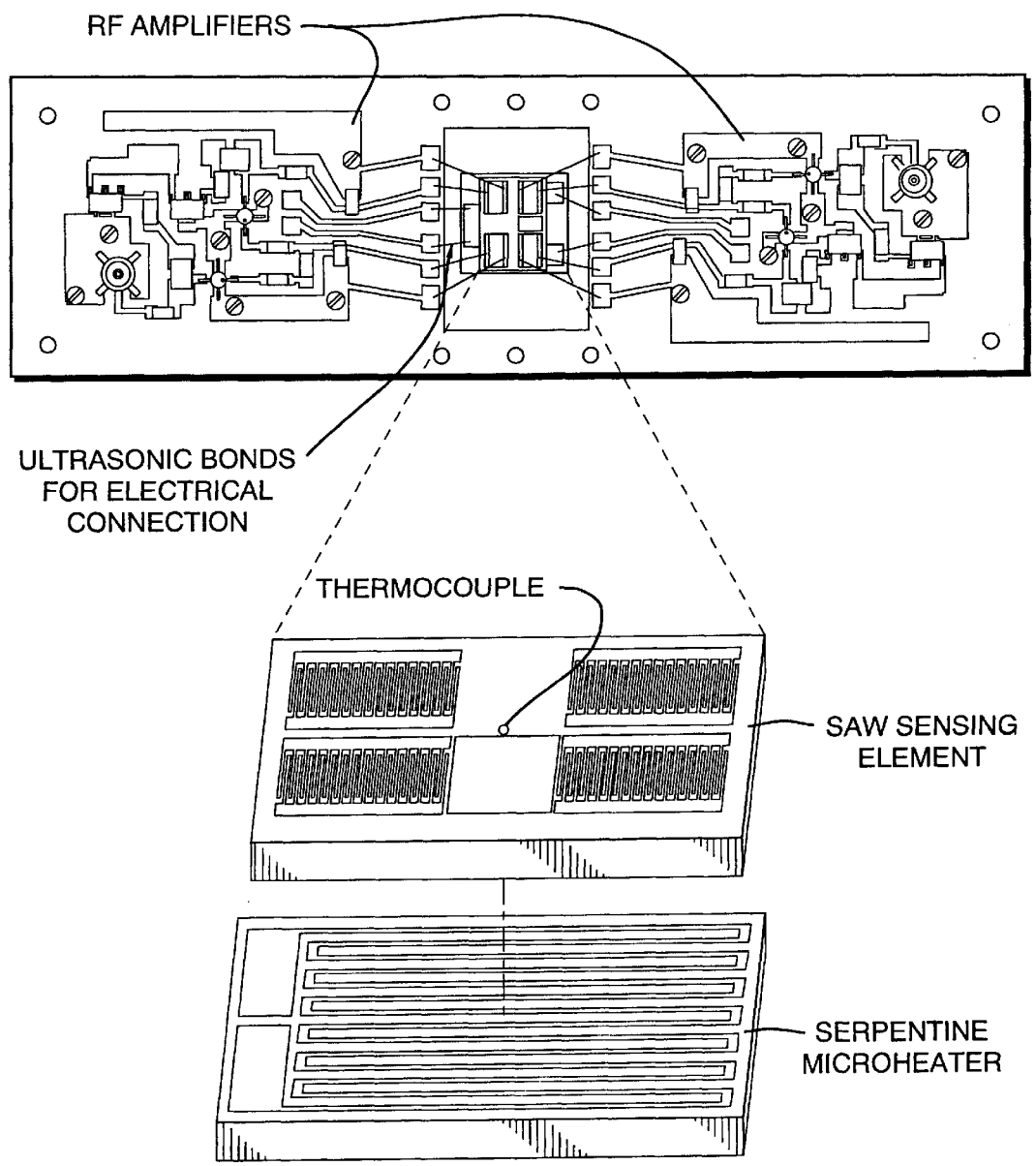
FIG. 3 is a schematic of a sensor in accordance with the present invention.

The surface acoustic wave sensor of the present invention also includes a serpentine microheater in thermal contact with the piezoelectric substrate as shown in FIG. 3. The serpentine microheater is preferably on a heater substrate having a suitable thickness, preferably wherein the piezoelectric substrate and the heater substrate each has a thickness of about 0.1 mm to about 1 mm.

In accordance with the present invention, the piezoelectric substrate is maintained at a temperature where mercury amalgamation-desorption kinetics occur in equilibrium.

An advantageous result of the present invention is that mercury desorbs spontaneously upon lowering of concentration due to higher operating temperatures within the range of about 100° C. to about 500° C. Most preferably, the sensor of the present invention is operated at temperatures of 125° C. or higher.

The present invention is also directed to a method for detection and measurement of gaseous mercury in air, which involves exposing a SAW delay line oscillator having a gold-coated delay path or SAW resonator with gold IDT and reflector structure to a gaseous environment having low concentrations of gaseous mercury; permitting the gaseous mercury to interact with the gold-coating so as to form an amalgam thereby changing film properties, such as nmass, elasticity, viscosity, and electrical conductivity and operating said sensor at a temperature sufficient so that gas-film reaction kinetics result in equilibrium between mercury amalgamation and desorption to result in an equilibrium value of amalgamated mercury that is dependent on gaseous elemental mercury gas concentration.

In accordance with the present invention, the environment comprises mercury emissions or mercury-compounding emissions which arise from a member selected from the group consisting of combustion processes, incineration processes, contaminated water, and contaminated soil.

The sensor of the present invention is based upon a SAW delay line oscillator with a gold-coated delay path, or a SAW resonator with gold IDT structure. In operation, gaseous mercury interacts rigorously with this gold coating or film, forming an amalgam. The resulting perturbation of film mechanical and electrical properties is manifested as a change in oscillation frequency. Measurement of gas concentration is achieved by operating the sensing element at a temperature where gas-film reaction kinetics result in an equilibrium between mercury amalgamation and desorption. This equilibrium value of amalgamated mercury is highly dependent upon the gas concentration. Thus, the delay line or resonator oscillation frequency is a sensitive measure of gaseous mercury concentration.

The present invention is suitable for detection of $Hg^0$ emission arising from combustion and incineration processes, as well as emissions from contaminated water and soil.

The sensor of the present invention is advantageous in that it measures concentration explicitly because of amalgamation-desorption equilibrium.

The following is a more detailed description of the present invention referring to the attached figures and the citations listed in the Appendix.

A sensor for the in situ detection and measurement of low concentrations of gaseous mercury is presented. The sensor is based upon a dual delay line SAW oscillator with a gold-coated delay path. Gaseous mercury interacts rigorously with the gold film, forming an amalgam The resulting increase in film mass is manifested as a decrease in oscillation frequency. Measurement of gas concentration is achieved by differentiating the sensor response at room temperature by operating the sensing element at a temperature where gas-film reaction kinetics result in equilibrium rates of mercury amalgamation and desorption. This equilibrium value of amalgamated mercury is highly dependent upon the gas concentration. Thus, the delay line oscillation frequency is a sensitive measure of gaseous mercury concentration.

Responses of this sensor to gaseous mercury concentrations in the ppb range are presented. The sensor response features are analyzed in terms of response shape, response magnitude, response time, and linearity at 25° C. and 200° C.

Mercury originating from nuclear fuel and weapons production and disposal, fossil fuel combustion and industrial processes is a major environmental pollutant that exists in air, soil, and groundwater. Mercury is particularly dangerous since it can bio-accumulate within the food chain and lead to irreversible neurological disorders and other health related problems.

Current laboratory techniques that are used to detect mercury a variety of elaborate separation strategies in conjunction with chromatographic, electrochemical or spectroscopic methods [1–6]. Although these techniques are sensitive, they are not appropriate for in situ monitoring, and typically samples must be collected and shipped to a central processing facility for analysis.

The most relevant work that has been done which might lead to a portable, in situ mercury sensor has utilized either chemiresistive or acoustic wave technology. McNerney et al [7] demonstrated that the resistance of a thin gold film changes upon exposure to mercury due to the formation of a mercury-gold amalgam. This chemiresistive sensor later led to a commercial sensor produced by Jerome Instruments [8]. This type of sensor utilizes a very thin gold film and has a limited dynamic range. Bristow [9] and, later, other investigators [10–16] demonstrated that a goldcoated quartz crystal microbalance (QCM) could also be used to detect mercury. In this configuration the resonant frequency of the QCM changes due to the added mass of mercury on the gold film. The major drawback of the QCM mercury sensor, however, is its relatively low sensitivity. Sauberlich et al

[17] proposed a design for a SAW-based sensor for mercury. An extensive examination of the literature, however, has not revealed any published data regarding this particular sensor design.

Figure 1:
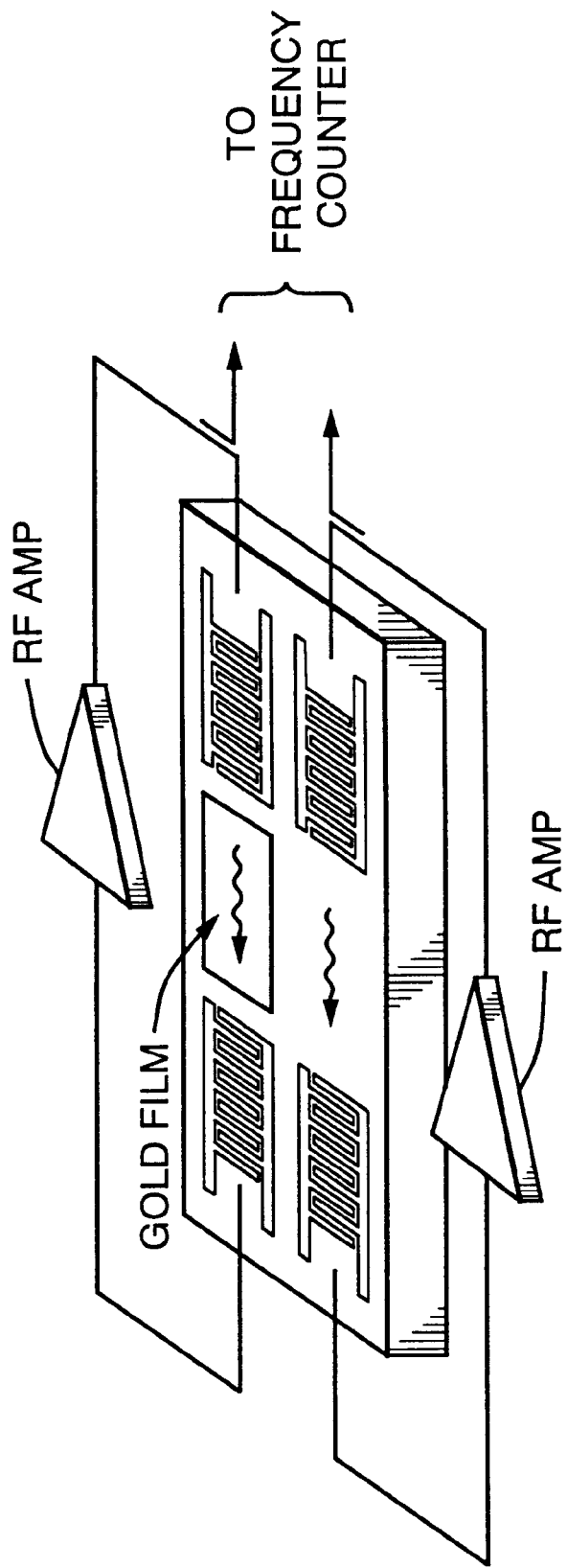
FIG. 1 is a schematic of a sensor in accordance with the present invention.

In the present paper, a SAW-based sensor which can potentially meet these requirements is presented. The device consists of a 261 MHz surface acoustic wave (SAW) dual delay line oscillator employing a 28° rotated Y-cut (RYC) quartz substrate and a 400 Å gold sensing film deposited upon one delay path. The other delay line is used as a reference to cancel extraneous environmental effects such as temperature fluctuations. Gaseous mercury readily amalgamates with the gold film, thus increasing its mass. Because the SAW is sensitive to mass changes, the difference frequency between the sensing and reference delay line oscillators becomes a sensitive measure of total amalgamated mercury. The sensor is shown in FIG. 1.

The behavior of the proposed SAW mercury sensor can be modelled using simplified perturbation theory [18]. This method results in a simple closed-form expression describing SAW frequency fluctuations due to perturbations of the mechanical and electrical properties of an overlay film In the case of the SAW mercury sensor, it can be assumed that electrical perturbations to the gold film have a negligible effect on the device frequency. The primary reason for this assumption is that the SAW is sensitive to electrical property changes only over a certain range of film sheet conductivity (about $10^{-6}$ to $10^{-8}$ Siemens for most SAW substates) [19]. Because the gold film acts like a short circuit, its conductivity is well out of this range. Hence, small changes in film conductivity will not perturb the sensor operating frequency. Mechanical perturbations that may affect the SAW include changes in film mass, elasticity, and viscosity. However, because the mercury-gold interaction takes place only at the surface of the film, elasticity and viscosity changes will not be as dominant as mass changes and, hence, will be neglected.

Figure 2:
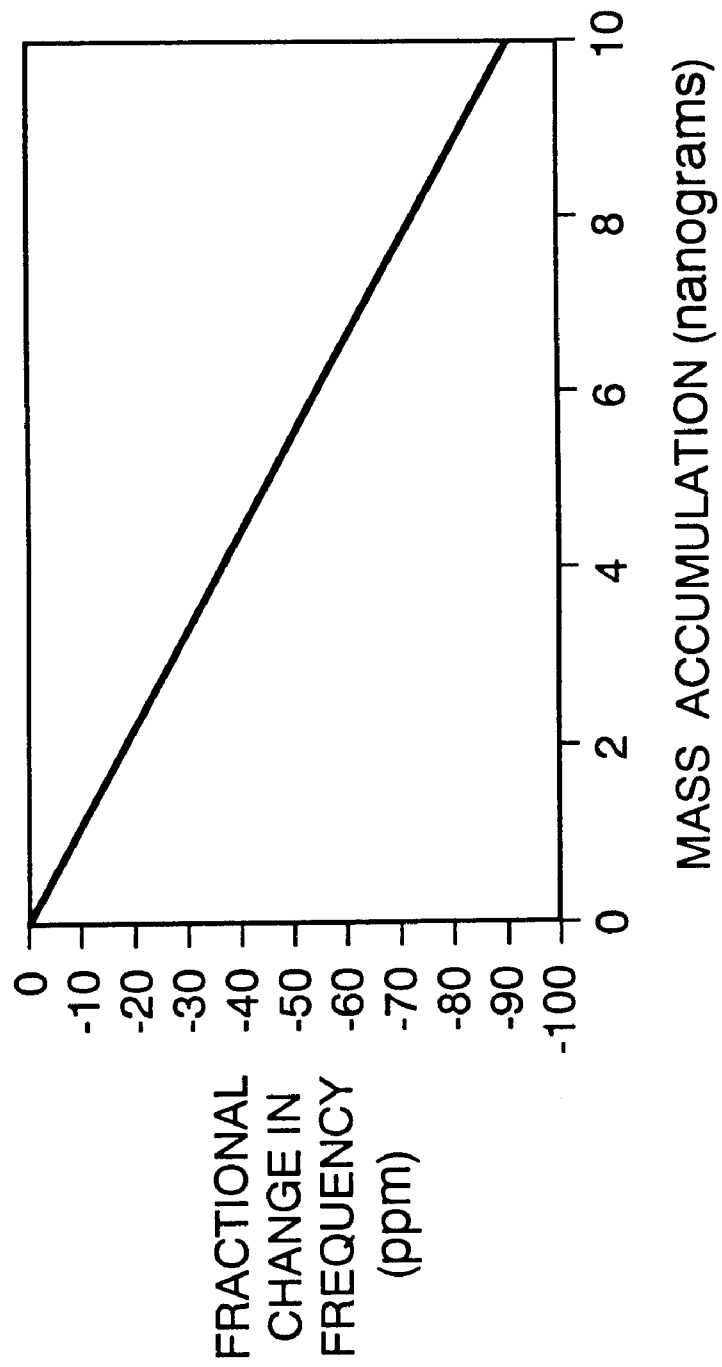
FIG. 2 is a chart showing fractional changes in operating frequency as a function of mass accumulation.

Assuming only film mass perturbations, the fractional change in frequency of the SAW delay line can be written as follows, $$\frac{\Delta f}{f} = \kappa(k_1 + k_2 + k_3)f\frac{\Delta m}{A}, \quad (1)$$

where $f$ is the nominal operating frequency of the device, $\kappa$ is the fractional coverage of the gold film (i.e. the fraction of the entire center-to-center distance of the SAW delay line that is coated with gold), $\kappa_n$ are the normalized surface particle velocities in the $x_n$ direction, $\Delta m$ is the change in mass, and A is the area of coverage. In FIG. 2 this relationship is plotted for the sensing element used in this work.

The prototype sensor designed and utilized in this work is shown in FIG. 3. The sensor consists of the SAW dual delay line sensing element described earlier, a serpentine microheater and thermocouple for temperature control, as well as all of the RF electronics required to maintain oscillation and provide a readable output.

Figure 4:
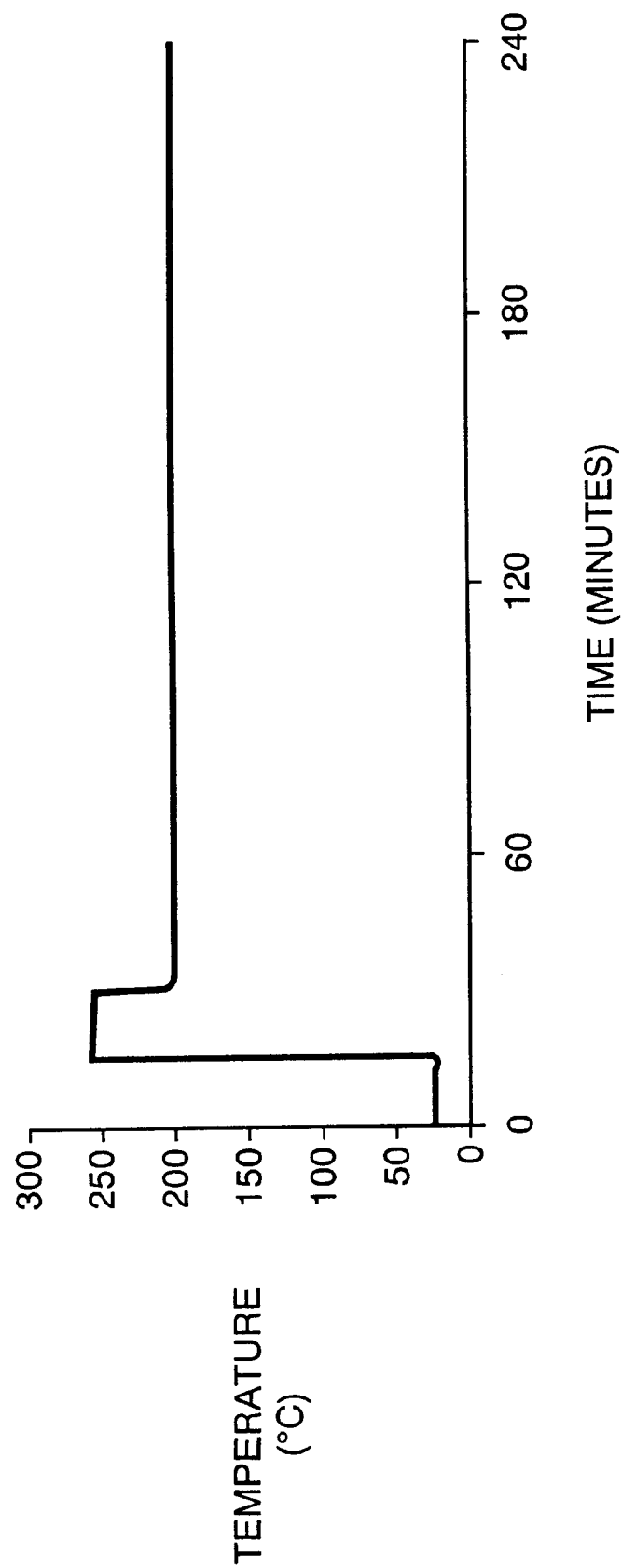
FIG. 4 is a chart of a temperature profile of the sensing element.
Figure 5:
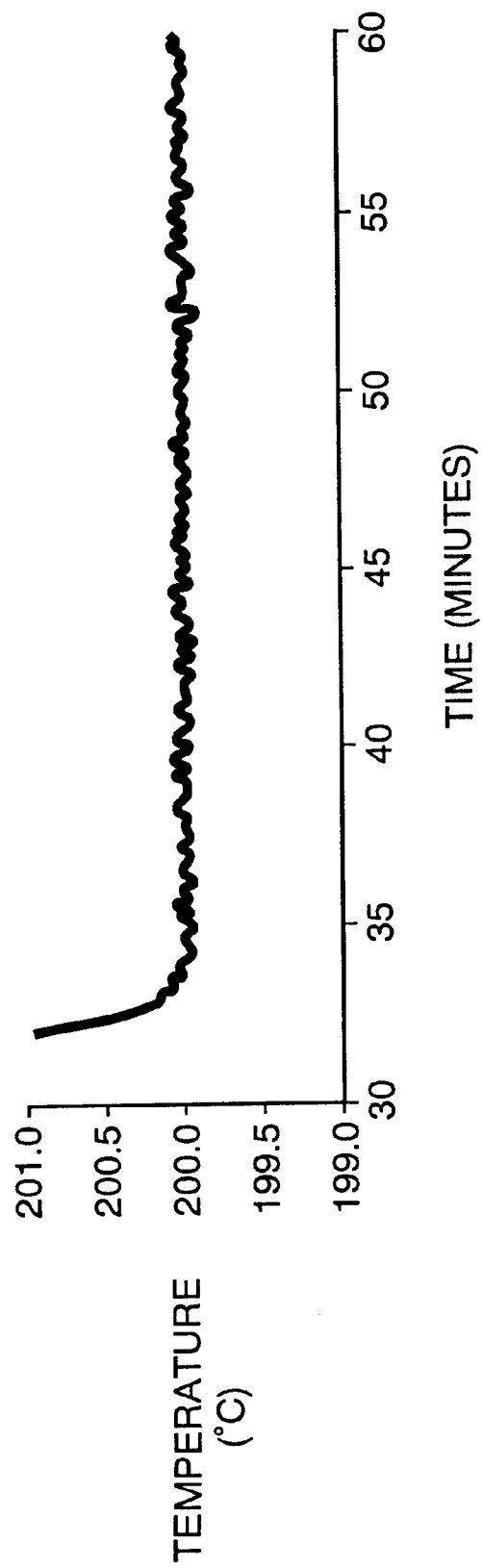
FIG. 5 is an expanded view of the temperature profile of FIG. 4.

The combination of the thermocouple, heating element, and a computer data acquisition system allow temperature to be controlled with high precision. FIG. 4 shows experimental data of a typical temperature profile of the sensing element during a test. The set point temperature is reached within 5 minutes and can be maintained within 0.05° C., as shown in FIG. 5.

Figure 6:
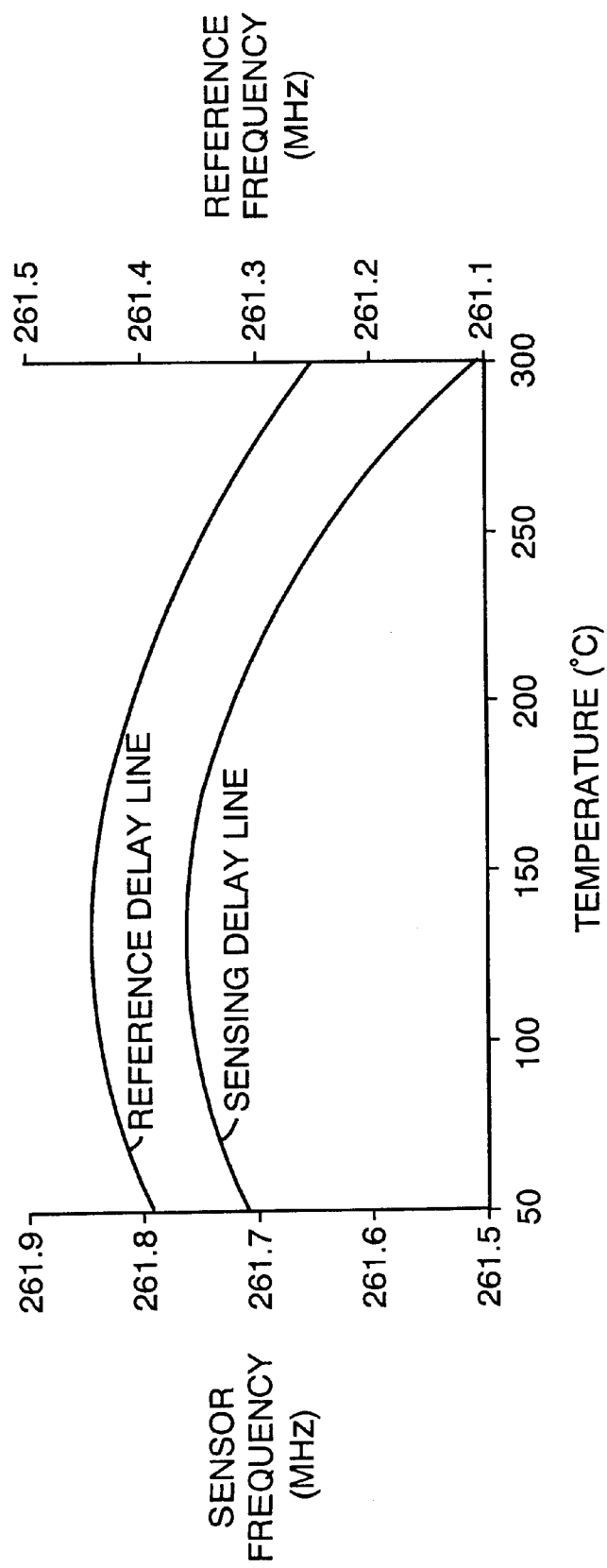
FIG. 6 is a graphic showing the frequencies of the sensing and reference delay lines matched, both exhibiting turnover temperatures of 130° C.
Figure 7:
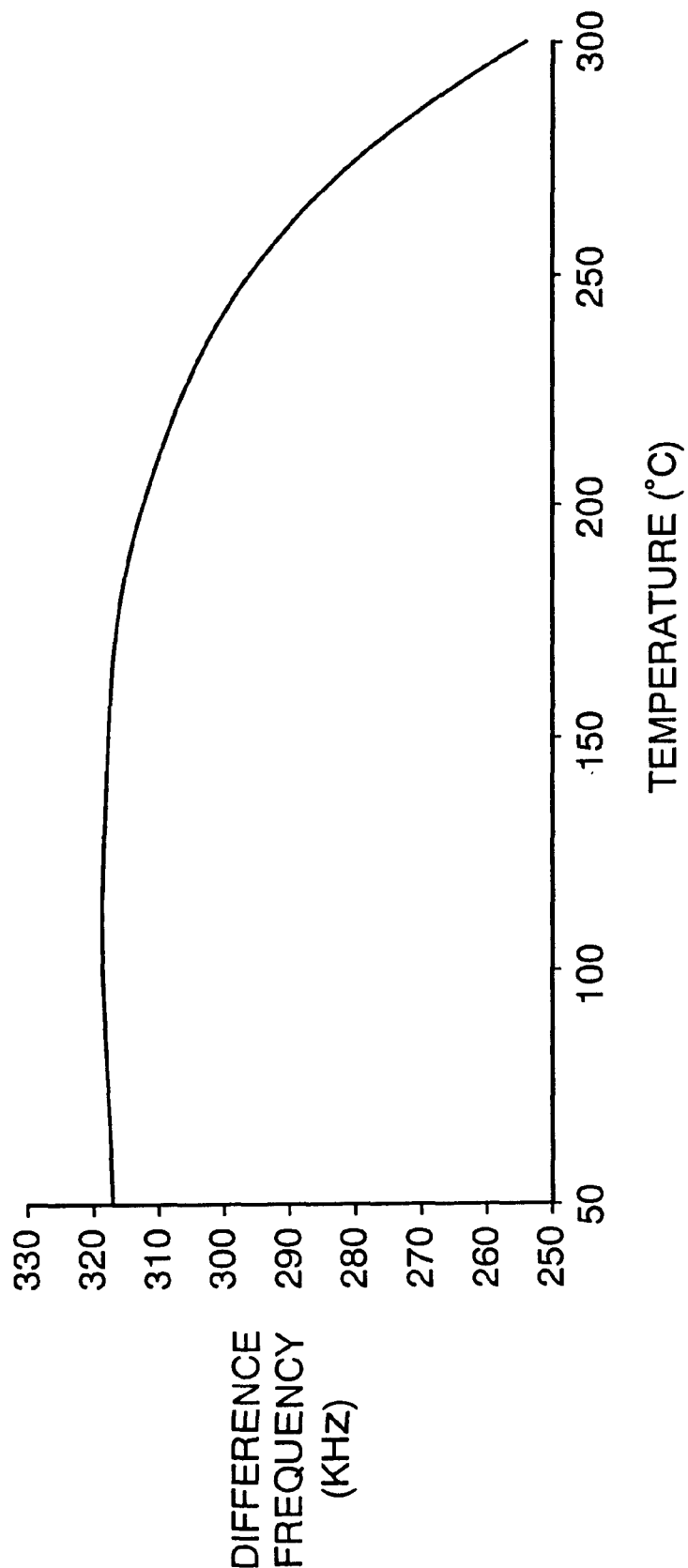
FIG. 7 is a graph showing the difference frequency exhibits near zero temperature coefficient over a range of 25 to 200° C.

The sensor has been designed for use over a range of temperatures from 25° C. to 250° C. 28° RYC quartz is used as the SAW substrate because its turnover temperature (where it exhibits zero temperature coefficient of frequency) is in the middle of this range, thus providing better temperature compensation over the whole range than more conventional substrates, such as ST quartz [20]. The gold film on the sensing delay path acts to lower the turnover temperature of that delay line. Therefore, an aluminum film is deposited onto the reference delay line to match its turnover temperature to that of the sensing delay line. The results are plotted FIG. 6. One can see that the turnover temperature of both delay lines are approximately 130° C. The resultant difference frequency is temperature compensated from 25° C. to about 200° C., as shown in FIG. 7.

Figure 8:
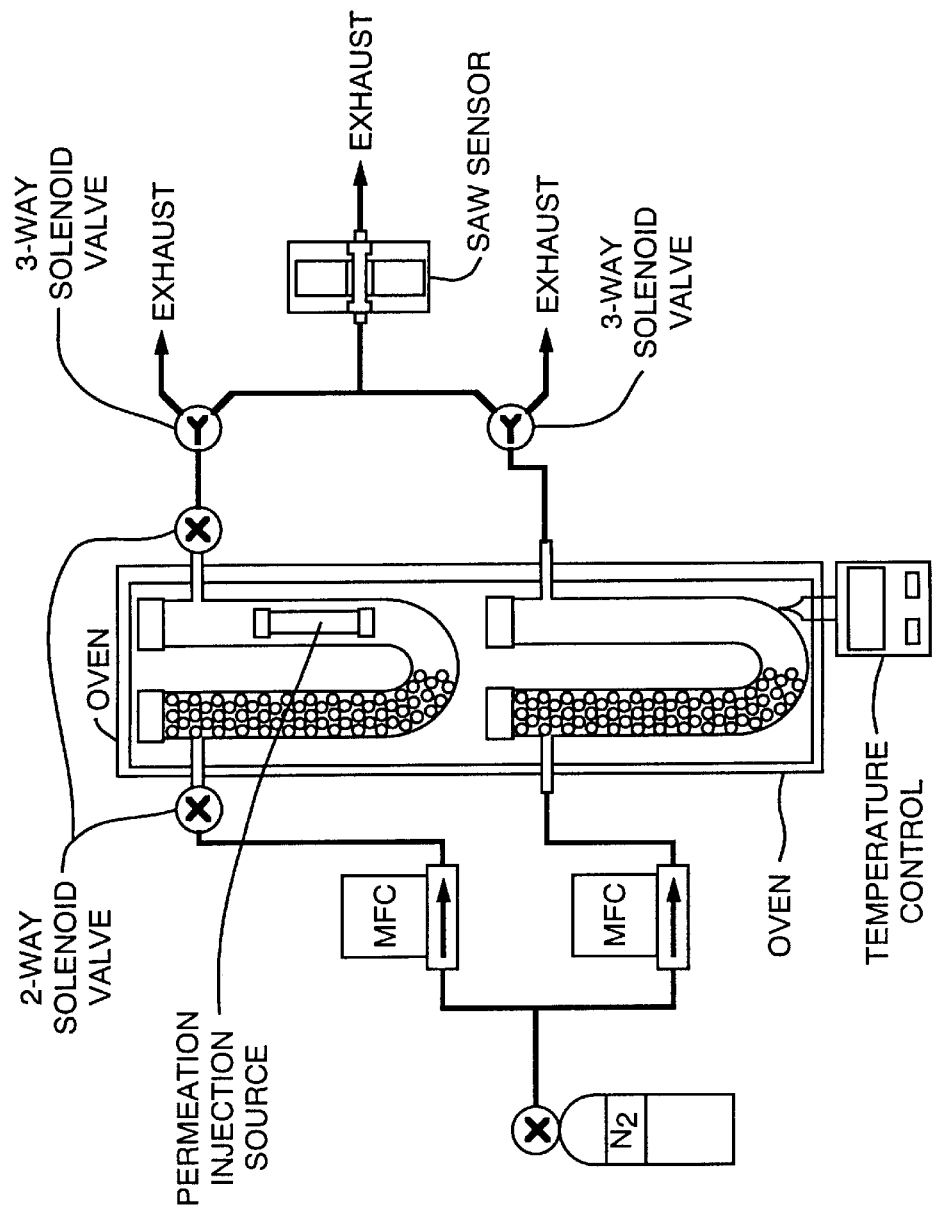
FIG. 8 is a schematic of the mercury gas delivery system.
Figure 9:
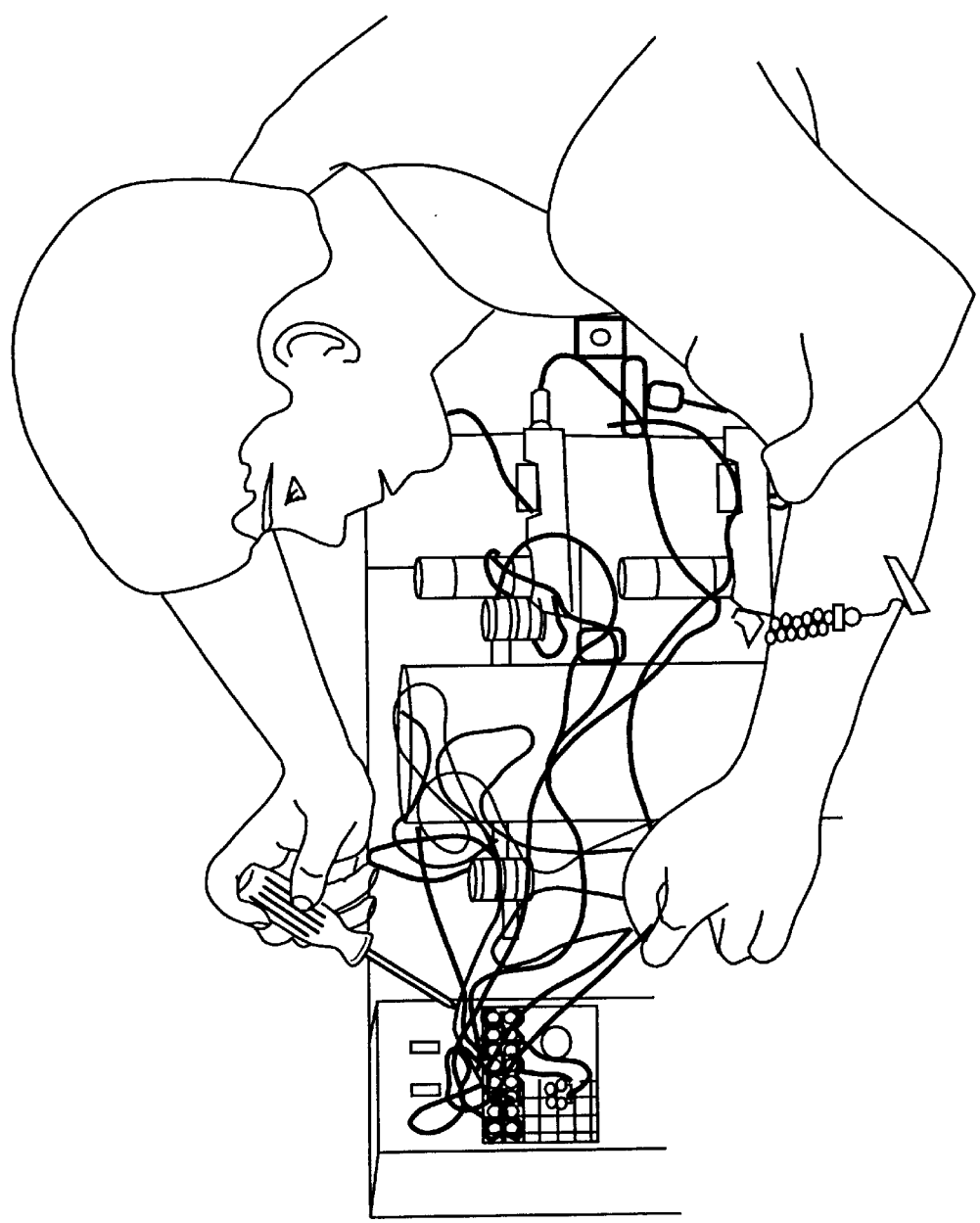
FIG. 9 is a photograph of the mercury gas delivery system.

The generation and delivery of gaseous mercury to the sensor is accomplished using a permeation injection source, an oven, and a system of valves and mass flow controllers, as shown in FIGS. 8 and 9. The permeation injection source is maintained at 100° C. in an oven. At this temperature, the source outputs mercury at a rate of 740 nanograms/minute. Dry nitrogen flows into the oven, through a glass bead heat exchanger, past the permeation injection source. Thus, by varying the flow rate of nitrogen through the tube, the mercury can be diluted to a particular concentration. A duplicate of this setup, without the permeation injection source, is used to deliver nitrogen without mercury. A pair of three-way valves is used to direct one of the two gas streams through the sensor.

Figure 10:
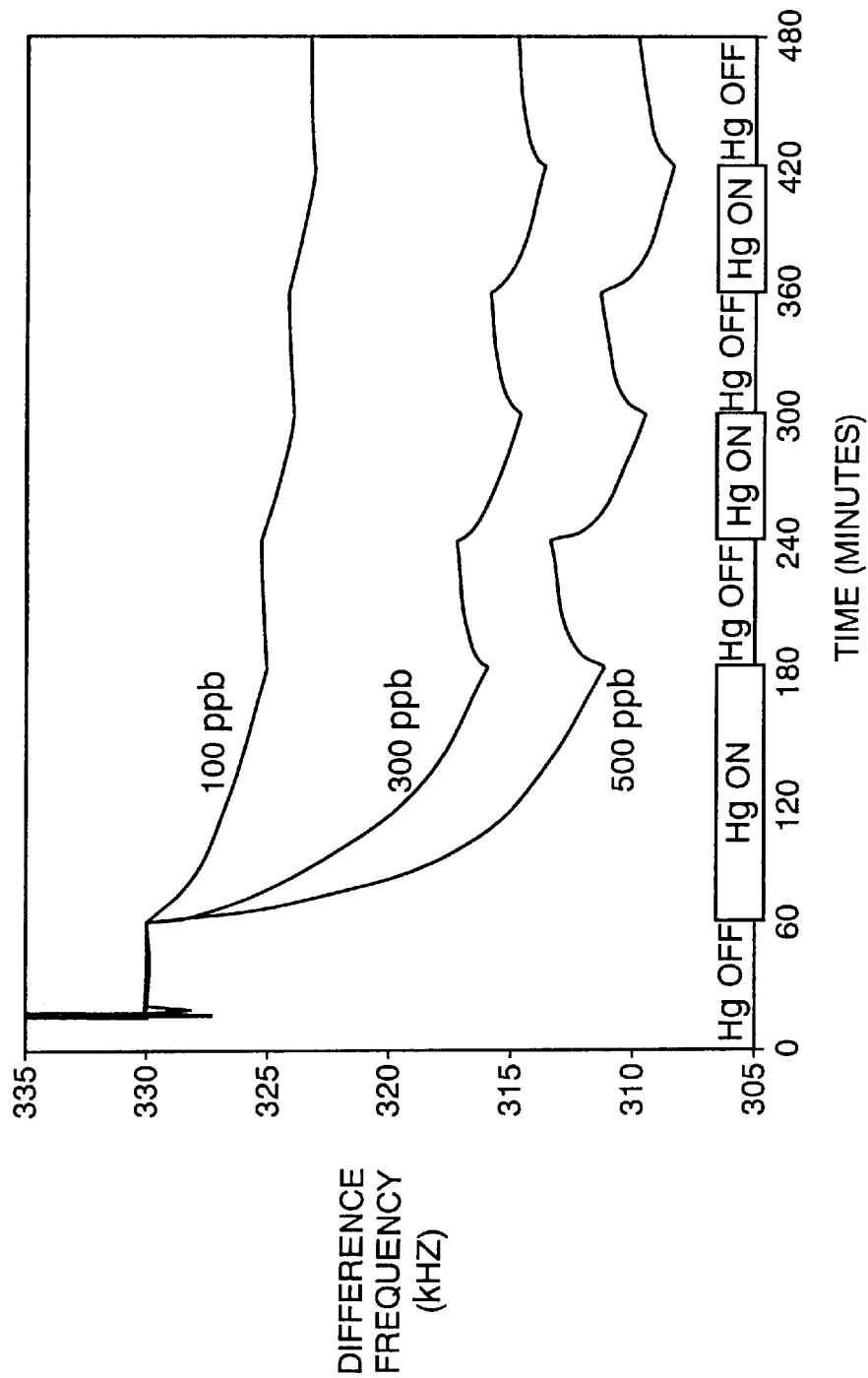
FIG. 10 is a graph showing the sensor to repeated exposures of 100, 300, and 500 ppb mercury at room temperature.

The response of the prototype sensor to repeated exposures of 100, 300, and 500 ppb at 25° C. is shown in FIG. 10. When operated at room temperature, the amalgamation process is essentially irreversible. Almost all of the mercury that comes into contact with the film sticks to it indefinitely, until the film becomes saturated. At this point, the film can be regenerated by heating it to a high temperature (i.e. 300° C.) for a few minutes to drive off the mercury. (This is the reason for the frequency spike during the first 15 minutes of the exposures of FIG. 10).

At 25° C. the sensor difference frequency changed by about 18.5 1 kHz (71 ppm) after 2 hours of exposure at 500 ppb. This corresponds to a mercury uptake of about 8 nanograms. With a total of 89 µg of mercury having passed by the device during that period of time, this corresponds to a collection efficiency of 0.009%.

Figure 11:
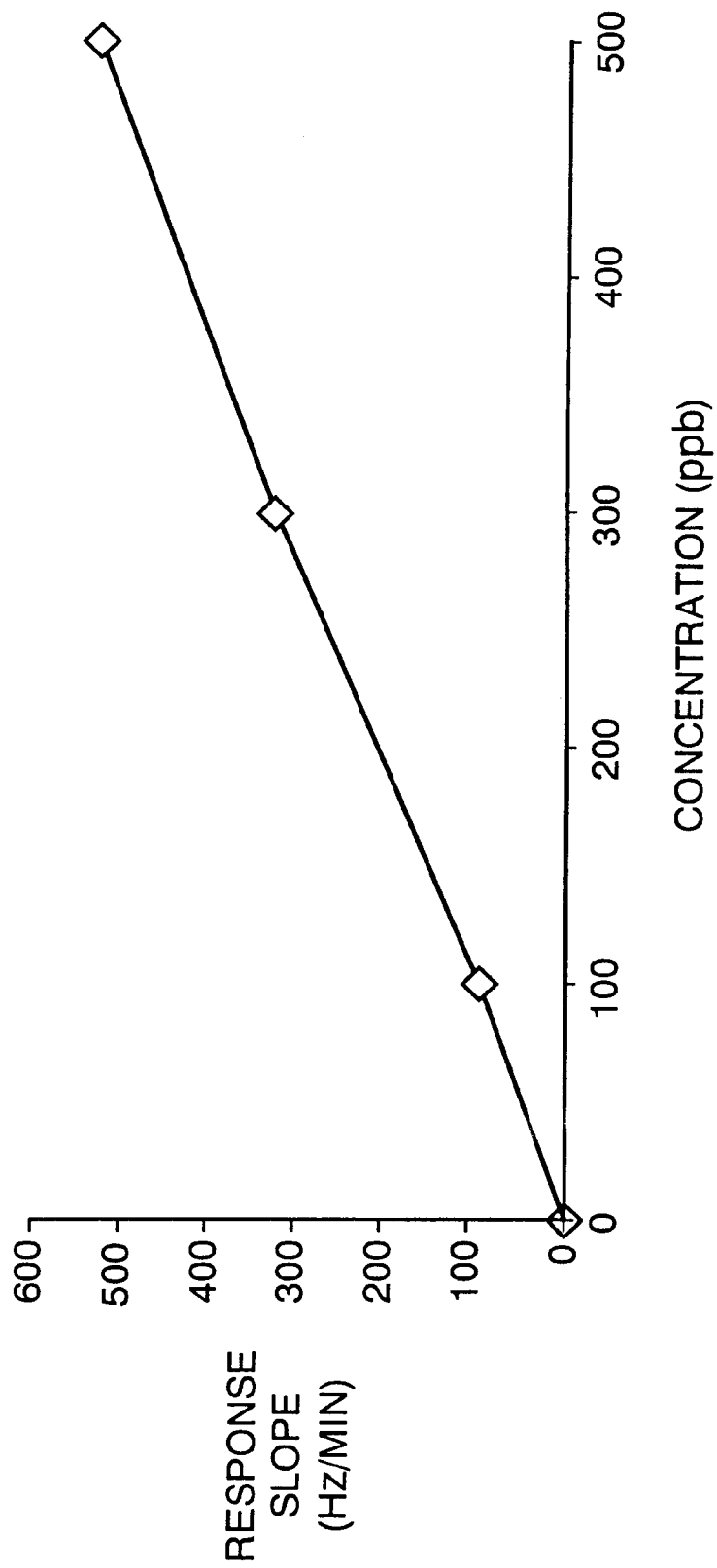
FIG. 11 is a graph showing the initial response slope as a function of mercury concentration for the prototype sensor at 25° C.

Because the pre-saturation response is basically the integral of the concentration, the response can be differentiated to measure concentration. The average response slope during the first ten minutes of exposure at 25° C. is plotted for 100, 300, and 500 ppb in FIG. 11. The response is linear with a slope of about 1.1 Hz/min.ppb.

Figure 12:
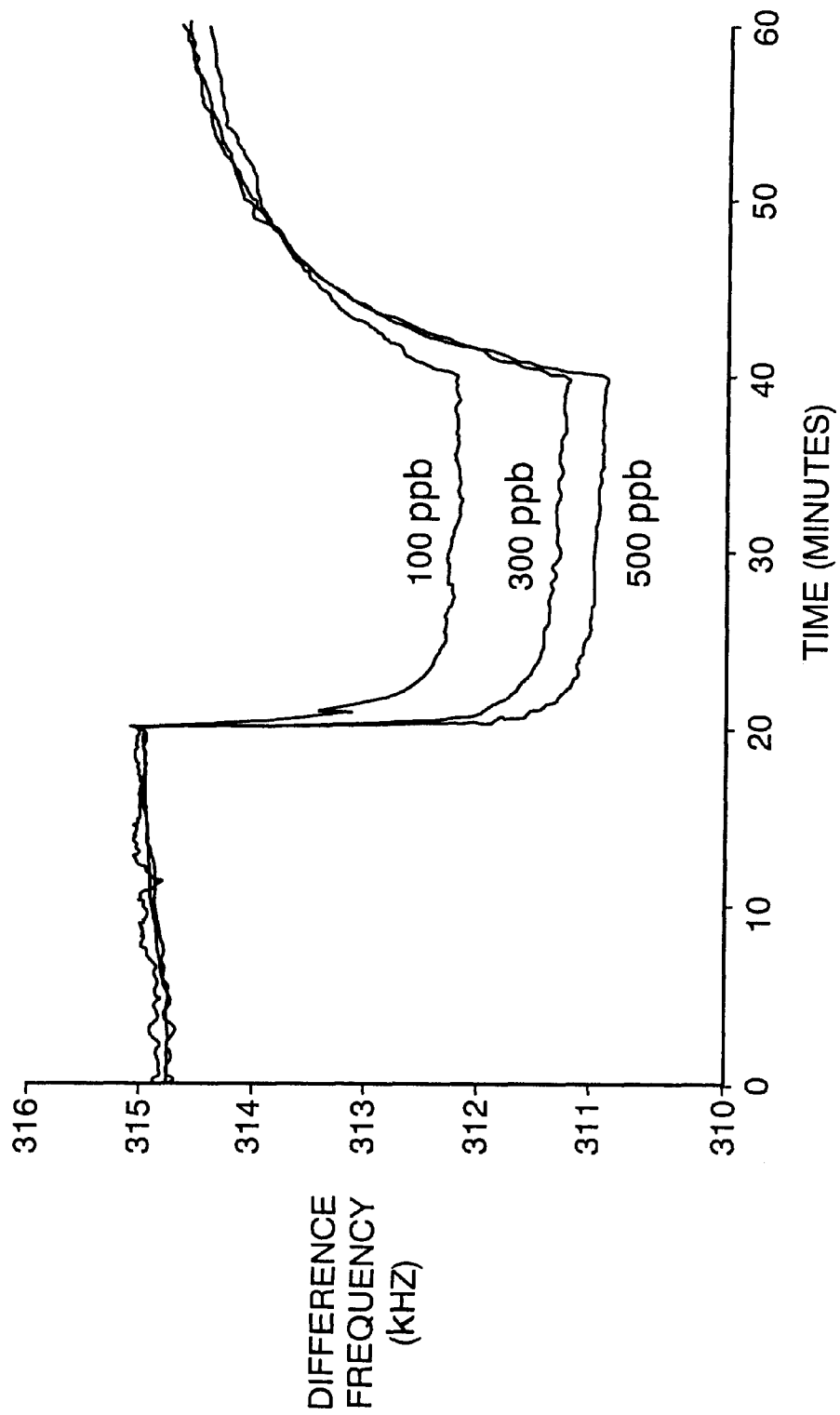
FIG. 12 is a graph showing the response of the prototype sensor to gaseous mercury concentrations of 100, 300, and 500 ppb at 200° C.

Looking carefully at FIG. 10, one can see that even at room temperature some mercury desorption occurs as the film approaches saturation. As stated earlier, at high temperatures (i.e. 300° C.) this phenomenon occurs much more rapidly and completely. The desorption rate is governed not only by the operating temperature, but also by the amount of mercury already amalgamated. In other words, the more mercury that has accumulated on the films the quicker the desorption rate. (This accounts for the "exponential decay" shape of the desorption curves in FIG. 10). Meanwhile, the rite of amalgamation is governed by the rate at which mercury molecules come into contact with the film, which is directly proportional to the concentration of the mercury in the gas. Therefore, at temperatures somewhere between 25 and 300° C., the rate of desorption is moderate and can exactly balance the rate of amalgamation. The equilibrium valve of amalgamated mercury at any time then becomes a direct measure of the mercury concentration. This is demonstrated experimentally at 200° C. in FIG. 12. Rather than measuring response slope and worrying about film saturation/regeneration, the response magnitude now becomes a direct measure of gas concentration, and no film regeneration is required. The response time of the sensor, when operated in this mode, is about two minutes. The recovery time is about 15 minutes.

Figure 13:
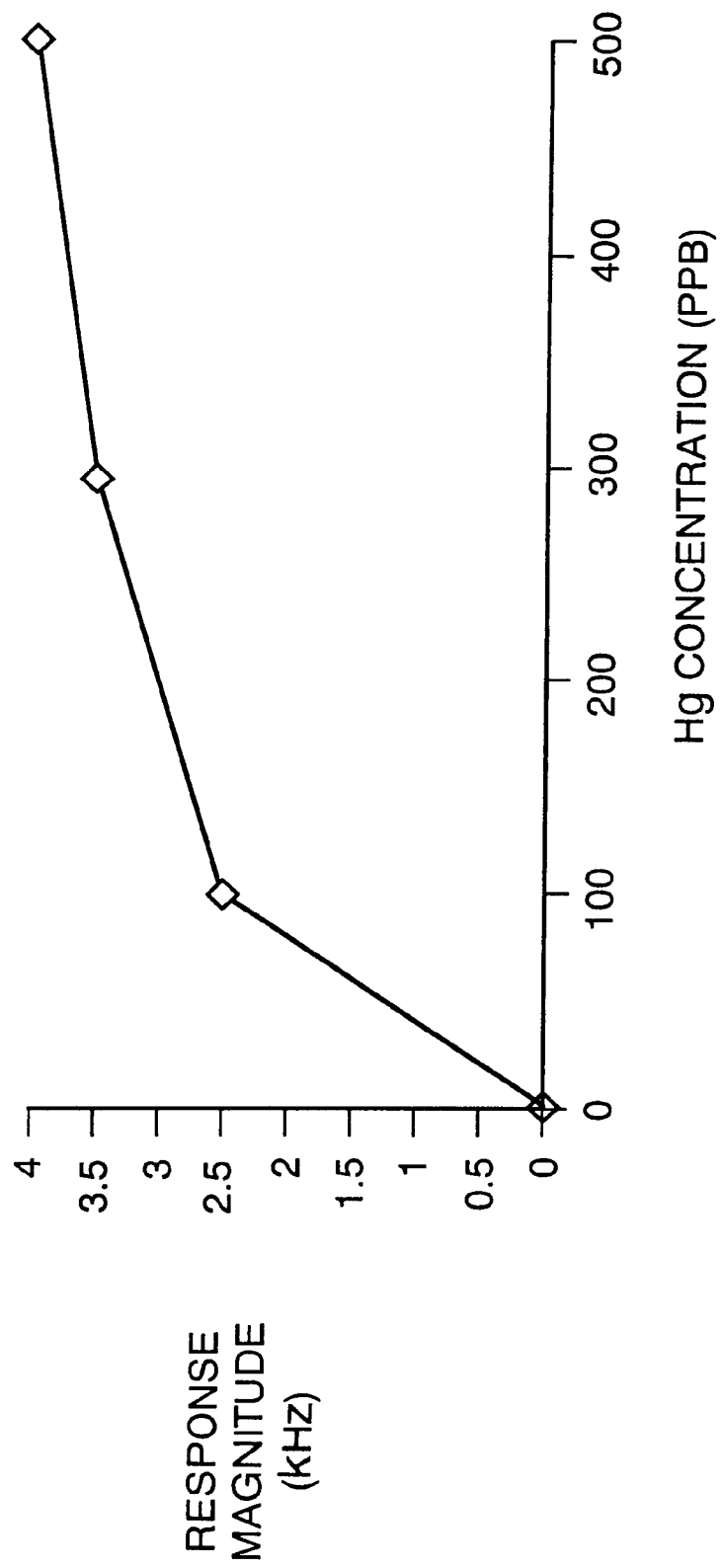
FIG. 13 is a graph showing the response magnitude of the sensor as a function of concentration at 200° C.

FIG. 13 shows the response magnitude as a function of gas concentration. It is apparent that the sensor does not exhibit the excellent linearity that it did at room temperature. However, it does demonstrate adequate resolution over the range of 0–500 ppb, with resolution increasing at lower concentrations.

A sensor for the detection and quantification of gaseous mercury has been presented. The sensor is based around a 261 MHz dual delay line SAW oscillator with a gold sensing film. The sensor responds reproducibly to gaseous mercury concentrations from 100 to 500 ppb. When operated at room temperature the sensor acts as an integrating element. The response is a direct measure of the total mercy with which the sensor has come into contact. The derivative of the response, therefore, is directly proportional to the mercury concentration. When operated in this mode, the sensing film eventually becomes saturated and must be regenerated by increasing the temperature. When operated at 200° C., the sensor response becomes a direct measure of instantaneous concentration, and periodic regeneration of the film is no longer required.

Future work on this sensor will include the examination of sensor response characteristics at other temperatures, the examination of lower concentrations of gaseous mercury, and the examination of the sensor response as a function of the thickness of the gold sensing film. Furthermore, the sensitivity of the sensor will be increased by fabricating the entire sensing interdigital transducer structure out of gold, rather than just a film over the delay path. The reference delay line may also be passivated with glass or silicon nitride to ensure that no mercury is reacting with the aluminum film.

EXAMPLE I

Responses of this sensor to gaseous mercury concentrations in the ppb range have been conducted, the results of which are shown in FIGS. 10, 11, 12, and 13.

EXAMPLE II

The sensor response features have been analyzed in terms of response time, recovery time, minimum detection limit, saturation detection limit, and linearity, as shown in FIGS. 10, 11, 12, and 13.

EXAMPLE III

The relationship between the sensor response and operating temperature have been investigated, as shown in FIGS. 10, 11, 12, and 13.

APPENDIX

1. R. Puk, J. Weber, "Critical Review of Analytical Methods for determination of Inorganic Mercury and Methylmercury compounds", *Appl. Orgmometallic Chem.*, 8, 296, 1994.
2. R. D. Jones, M. E. Jacobson, R. Jaffe, J. West-Thomas, C. Arfstrom, A. Alli, "Method Development and Sample Processing of Water, Soil, and Tissue for the Analysis of Total and Organic Mercury by Cold Vapor Atomic Fluorescence Spectrometry", 80, 1285, 1995.
3. M. Aceto, A. Foglizzo, E. Mentasti, G. Sacchero, C. Sarzaini, "Mercury Speciation in Biological Samples", 60, 1–13, 1995.
4. M. Schintu, F. Jean-Caurant, J-C. Amiard, "Organomercury Determination in Biological Reference Materials: Application to a Study on Mercury Speciation in Marine Mammals off the Faoe Islands", *Ecotox. Envir. Safety*, 24, 95, 1992.
5. S. Rapsomanikus, M. Andreae, "New Speciation Approaches in the Biogeochemical Cycles of Organometallics in the Environment", *Intern. J. Environ. Chem.*, 49, 43, 1992.

APPENDIX

6. R. Puk, J. Weber, "Determination of Mercury(II), Monomethylmercury Cation, Dimethylmercury and Diethylmercury By Hydride Generation, Cryogenic Trapping and Atomic Absorption Spectrometric Detection", *Anal. Chem. Acta.*, 292, 175, 1994.
7. J. J. McNermy, P. R. Buseck and R. C. Hanson, "Mercury Detection by Means of Thin Gold Film", *Science*, 178, 611. 1972.
8. Jerome Division of Arizona Instruments, Product Literature.
9. Q. Bristow "An Evaluation of the Quartz Crystal Microbalance as a Mercury Vapor Sensor for Soil Gases", *J. Geochem. Expl.*, 55, 1972.
10. E. P. Scheide and J. K. Taylor, "Piezoelectric Sensor for Mercury in Air", *Environmental Science and Technology*, 8, 1097, 1974.

APPENDIX

11. E. P. Scheide and J. K. Taylor, "A Piezoelectric Crystal Dosimeter for Monitoring Mercury Vapor in Industrial Atmospheres", *Am. Ind. Hygiene Ass. Journal*, Dec. 1975.
12. E. P. Scheide and R. B. J. Warner, "A Piezoelectric Crystal Mercury Monitor", ibid, 745, September, 1978.
13. E. P. Scheide, "The Piezoelectric Crystal Mercury Dosimeter", *Research Frontier*, 47, January 1977.
14. M. H. H., G. G. Guilbault and E. P. Scheide, "Determination of Nanogram Quantities of Mercury in Water with a Gold-Plated Piezoelectric Crystal Detector", *Anal. Chem. Act.*, 130, 141, 1981.
15. A. N. Mogilevski, A. D. Mayorov, N. S. Stroganova, D. B. Stavrovsli, L. P. Galkina, L. Spassov, D. Mihailou and R. Zahariera, "Measurement of the Concentron of Mercury Vapor in Air through a Piezoresonance Method", Sensors and Actuators A 28, 35, 1991.

APPENDIX

16. L Spassov, D. Y. Yankov, A. N. Mogilevski and A. D. Mayorov, "Piezoelectric sorption Sensor for Mercury Vapors in Air Using a Quartz Resonator", Rev. Sci. Instru. 64, 225, 1993.
17. R. Sauberlich, P. Petter, W. Buff, B. Wall and N. Nindel, "Method and Device for the Concentraton of Mercury in Gases", Patent 00268530A1, Deutsche Demokrache Republik (1989).
18. B. A. Auld, "Acoustic Fields and Waves in Solids" Vol II, Wiley Interscience Publication, 1973.
19. R. Lec, R. S. Falconer, Z. Xu, and J. F. Vetelino, "Macroscopic Theory of Surface Acoustic Wave Gas Microsensors", 1988 IEEE Ultrasonics Symposium, Chicago, Ill., pp 585–589.
20. J. J. Caron, J. C. Andle and J. F. Vetelino, "Surface Acoustic Wave Substrates for High Temperature Applications", 1996 IEEE Intl. Freq. Ctrl. Symp., Honolulu, HI, pp. 222–227 (1996).

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. A surface acoustic wave (SAW) sensor system for measuring mercury vapor concentrations in a gaseous environment, the system comprising:
   a. a SAW delay-line oscillator, wherein said SAW delay-line oscillator includes:
      i. a piezoelectric substrate;
      ii. a sensing delay line formed to include a material with which mercury amalgamates; and
      iii. a reference delay line formed of a material with which mercury does not amalgamate;
   b. oscillator circuitry and a frequency counting means coupled to said sensing delay line and to said reference delay line for measuring changes in a frequency of a first signal through said sensing delay line and a frequency of a second signal through said reference delay line as the gas containing mercury contacts said sensing delay line and said reference delay line, wherein changes in the frequency of said first signal are used to determine a mercury vapor concentration in the gaseous environment; and
   c. heating means coupled to said SAW delay-line oscillator for regulating a temperature of said sensing delay line and said reference delay line.

2. The system as claimed in claim 1 wherein said material of said sensing delay line is selected from the group consisting of: gold, silver, and copper.

3. The system as claimed in claim 2 further comprising a temperature measuring device connected to said piezoelectric substrate and, as part of said heating means, a serpentine microheater, wherein said temperature measuring device and said serpentine microheater are used in combination to measure and control a temperature of said piezoelectric substrate.

4. The system as claimed in claim 3 wherein said piezoelectric substrate has a thickness in the range of about 0.1 mm to about 1 mm.

5. A surface acoustic wave (SAW) sensor system for measuring mercury vapor concentrations in a gaseous environment, the system comprising:
   a. a SAW device having a piezoelectric substrate and a surface including a signal path, wherein a material with which mercury amalgamates is applied to said surface of said SAW device at least on said signal path;
   b. oscillator circuitry and a frequency counting means coupled to said signal path of said SAW device for measuring changes in a frequency of a signal through said signal path as the gas containing mercury contacts said signal path, wherein changes in the frequency of said signal are used to determine a mercury vapor concentration in the gaseous environment; and
   c. heating means coupled to said SAW device for regulating a temperature of said signal path.

6. The system as claimed in claim 5 wherein said material is selected from the group consisting of: gold, silver, and copper.

7. The system as claimed in claim 6 further comprising a temperature measuring device connected to said piezoelectric substrate and, as part of said heating means, a serpentine microheater, wherein said temperature measuring device and said serpentine microheater are used in combination to measure and control a temperature of said piezoelectric substrate.

8. A process for measuring the concentration of mercury vapor in a gaseous environment, the process comprising the steps of:
   a. coupling an oscillator circuit and a frequency counting means to a signal path on a surface of a surface acoustic wave (SAW) device, wherein said signal path includes a material with which mercury amalgamates;
   b. directing an oscillatory signal through said signal path of said SAW device;
   c. contacting a mercury-vapor-containing gas with said signal path;
   d. regulating with heating means a temperature of said signal path as said mercury-vapor-containing gas contacts said signal path; and
   e. determining mercury vapor concentration in said gaseous environment as a function of the frequency of said oscillatory signal through said signal path.

9. The process as claimed in claim 8 wherein the heating means includes a serpentine microheater coupled to a piezoelectric substrate of said SAW device.

10. The process as claimed in claim 9 further comprising the step of regulating the operation of said serpentine microheater to ensure that said piezoelectric substrate is maintained substantially at its turnover temperature.

11. The process as claimed in claim 9 further comprising the step of regulating the operation of said serpentine microheater to ensure that said material is at a temperature to ensure that mercury amalgamation/desorption kinetics are substantially at equilibrium.

12. The process as claimed in claim 9 wherein said serpentine microheater is operated to maintain the temperature of said piezoelectric substrate is selected to be in the range of about 100° C. to about 500° C.

13. The process as claimed in claim 8 wherein said SAW sensing device is a SAW delay-line oscillator.

14. The process as claimed in claim 8 wherein said material is selected from the group consisting of gold, silver, and copper.

* * * * *